United States Patent
Matsuzaki et al.

(10) Patent No.: US 6,681,129 B2
(45) Date of Patent: Jan. 20, 2004

(54) SURGICAL OPERATION NAVIGATION APPARATUS AND METHOD

(75) Inventors: Hiroshi Matsuzaki, Hachioji (JP); Akito Saito, Hino (JP); Yukihito Furuhashi, Hachioji (JP); Takao Shibasaki, Tokyo (JP)

(73) Assignee: Olympus Optical Co., Ltd., Tokyo (JP)

( * ) Notice: Subject to any disclaimer, the term of this patent is extended or adjusted under 35 U.S.C. 154(b) by 279 days.

(21) Appl. No.: 09/966,972

(22) Filed: Sep. 28, 2001

(65) Prior Publication Data

US 2002/0042566 A1 Apr. 11, 2002

(30) Foreign Application Priority Data

Sep. 29, 2000 (JP) ........................................ 2000-301441

(51) Int. Cl.[7] ................................................. A61B 5/05
(52) U.S. Cl. ...................................................... 600/407
(58) Field of Search ................................. 600/407–471, 600/587; 128/897, 898, 916, 920, 899; 382/171, 177, 218, 159, 278, 131, 228, 288, 196; 606/130, 129, 151, 139; 707/1, 10; 378/165, 205, 206, 207

(56) References Cited

U.S. PATENT DOCUMENTS 5,825,908 A  * 10/1998  Pieper et al. ................ 382/131
6,167,296 A  * 12/2000  Shahidi ....................... 600/427
6,226,548 B1 *  5/2001  Foley et al. ................. 600/426
6,236,875 B1 *  5/2001  Bucholz et al. ............. 600/407
6,379,302 B1 *  4/2002  Kessman et al. ........... 600/437

FOREIGN PATENT DOCUMENTS

JP  09-173352  7/1997
JP  10-005245  1/1998

* cited by examiner

Primary Examiner—Ali M. Imam
(74) Attorney, Agent, or Firm—Frishauf, Holtz, Goodman & Chick, P.C.

(57) ABSTRACT

A surgical operation navigation apparatus comprises a medical image storage section that stores three-dimensional information of a subject measured by a medical image diagnosis unit. A modification information storage section modifies and stores the three-dimensional information of the subject based on predicted modification of the subject. A morphological shape measuring instrument measures a three-dimensional morphological shape of the subject. A morphological shape information storage section compares a three-dimensional morphological shape of a subject with three-dimensional information, and selects and outputs three-dimensional information of the subject that is the most analogous to the morphological shape of the subject. A data image generating section generates data image from the selected, outputted three-dimensional information of the subject. An image superimposing section superimposes a data image from the data image generation section and an image of the subject from the surgical operation utensil, and outputs the superimposed image to an image display device.

26 Claims, 5 Drawing Sheets

SURGICAL OPERATION NAVIGATION APPARATUS AND METHOD

CROSS-REFERENCE TO RELATED APPLICATIONS

This application is based upon and claims the benefit of priority from the prior Japanese Patent Application No. 2000-301441, filed Sep. 29, 2000, the entire contents of which are incorporated herein by reference.

BACKGROUND OF THE INVENTION

1. Field of the Invention

The present invention relates to a surgical operation navigation apparatus and method.

2. Description of the Related Art

Conventionally, a slice image at a periphery of a diseased site is acquired by a tomographic image acquisition technique such as CT or MRI prior to surgical operation, and surgical operation navigation is carried out by using a three-dimensionally reconstructed image using a technique such as computer graphics.

In addition, during surgical operation, a slice image is acquired as a real time monitor image by a technique such as mobile CT or open MRI.

For example, Jpn. Pat. Appln. KOKAI Publication No. 9-173352 discloses a medical navigation system for displaying a correlation between a specified region of the inside or surface of a patient body corresponds and a region on a medical image, making it possible to easily grasp the correlation between them. In addition, Japanese Patent Application Laid-open No. 10-5245 discloses a surgical operation assisting apparatus comprising blood vessel sensing section for sensing a blood vessel in the vicinity of a tip end of a surgical operation utensil and notification section for notifying to an operator the blood vessel sensed by this blood vessel sensing section, thereby reducing a burden of the operator during surgical operation.

However, a real time monitor image acquired by intra-operative image acquisition cannot be generally acquired as a high definition image as compared with a post-operative image. Thus, it is considered to use a high definition image acquired prior to surgical operation, but the morphological shape of a diseased site is slightly modified post-operatively or intra-operatively. Therefore, the pre-operatively acquired high definition image could not be used as an intra-operative image of a diseased site as is.

BRIEF SUMMARY OF THE INVENTION

The present invention has been made in order to solve the foregoing problem. It is an object of the present invention to provide a surgical operation navigation apparatus and method for modifying and storing a pre-operatively acquired high definition image of a diseased site, thereby making it possible to carry out surgical operation in real time using a high definition image of the diseased site during surgical operation as well.

In order to achieve the foregoing object, according to a first aspect of the present invention, there is provided a surgical operation navigation apparatus, comprising:

medical image storage section for storing three-dimensional information of a subject measured by medical image diagnosis apparatus;

modification information storage section for modifying and storing three-dimensional information of a subject stored in the medical image storage section based on predicted modification of the subject;

morphological shape measuring instrument for measuring a three-dimensional morphological shape of the subject;

position/posture detecting section for detecting a subject and a position/posture of a surgical operation utensil that carries out observation of the subject;

modified morphological shape selecting section for comparing a three-dimensional morphological shape of the subject measured by the morphological shape measuring instrument with three-dimensional information stored in the modification information storage section, thereby selecting and outputting three-dimensional information of the subject which is the most analogous to a morphological shape of the subject from the modification information storage section;

data image generating section for generating data image from the selected, outputted three-dimensional information of the subject; and image superimposing section for superimposing the data image from the data image generating section and the image of the subject from the surgical operation utensil on each other, thereby outputting the superimposed image to an image display device.

According to a second aspect of the present invention, there is provided a surgical operation navigation apparatus, comprising:

medical image storage section for storing three-dimensional information of a subject measured by a medical image diagnosis apparatus;

modification information storage section for modifying and storing three-dimensional information of the subject stored in the medical image storage section based on predicted modification of the subject;

morphological shape measuring instrument for measuring a three-dimensional morphological shape of the subject;

position/posture detecting section for detecting a subject and a position/posture of a surgical operation utensil that carries out observation of the subject;

morphological shape information sampling section for sampling three-dimensional morphological shape information on a site that corresponds to the field of view of the surgical operation utensil from three-dimensional morphological shape information of the subject measured by the morphological shape measuring instrument based on position/posture information on a surgical operation utensil from the position/posture detecting section;

modification information sampling section for sampling three-dimensional morphological shape information on a site tat corresponds to the field of view of the surgical operation utensil from the modification information storage section based on position/posture information on the surgical operation utensil from the position/posture section;

modification information selecting section for comparing the morphological shape information sampling section with three-dimensional morphological shape information from the modification information sampling section, thereby selecting from the modification information sampling section a three-dimensional shape that is the most analogous to the morphological shape information from the morphological shape information sampling section;

data image generating section for generating data image from the selected, outputted three-dimensional morphological shape information of the subject; and image superimposing section for superimposing data image from the data image generating section and an image of the subject from the surgical operation utensil on each other, followed by outputting the superimposed image to an image display device.

According to a third aspect of the present invention, there is provided a surgical operation navigation apparatus, comprising:

medical image storage section for storing three-dimensional information of a subject measured by a medical image diagnosis apparatus;

modification information storage section for modifying and storing three-dimensional information of the subject stored in the medical image storage section based on predicted modification of the subject;

morphological shape measuring instrument for measuring a three-dimensional morphological shape of the subject;

position/posture detecting section for detecting a subject and a position/posture of a surgical operation utensil that carries out observation of the subject;

two-dimensional morphological shape information sampling section for sampling two-dimensional morphological shape information on a site that corresponds to the field of view of the surgical operation utensil from three-dimensional morphological shape information of the subject measured by the morphological shape measuring instrument based on position/posture information on a surgical operation utensil from the position/posture detecting section;

two-dimensional modification information sampling section for projecting the site that corresponds to the field of view of the surgical operation utensil from the modification information storage section, and then, sampling two-dimensional morphological shape information based on position/posture information on the surgical operation utensil from the position/posture detecting section;

modification information selecting section for comparing two-dimensional morphological shape information from the two-dimensional morphological shape information sampling section and the two-dimensional modification information sampling section with each other, selecting two-dimensional modification information that is the most analogous to two-dimensional morphological shape information from the two-dimensional morphological shape information sampling section, and then, outputting three-dimensional morphological shape information that corresponds to the two-dimensional modification information;

data image generating section for generating data image from the selected, outputted three-dimensional morphological shape information of the subject; and image superimposing section for superimposing the data image from the data image generating section and the image of the subject from the surgical operation utensil on each other, followed by outputting the superimposed image data to an image display device.

According to a fourth aspect of the present invention, there is provided a surgical operation navigation method, comprising the steps of:

storing three-dimensional information of a subject measured by a medical image diagnosis apparatus;

modifying and storing the stored three-dimensional information of a subject based on predicted modification of the subject;

measuring a three-dimensional morphological shape of the subject;

detecting a subject and a position/posture of a surgical operation utensil that carries out observation of the subject;

comparing the measured three-dimensional morphological shape of the subject with the stored three-dimensional information, thereby selecting and outputting three-dimensional information of the subject which is the most analogous to a morphological shape of the subject;

generating data image from the selected, outputted three-dimensional information of the subject; and superimposing and displaying the generated data image from the data image generating section and the image of the subject from the surgical operation utensil on each other.

According to a fifth aspect of the present invention, there is provided a surgical operation navigation method, comprising the steps of:

storing three-dimensional information of a subject measured by a medical image diagnosis apparatus;

modifying and storing the stored three-dimensional information of the subject based on predicted modification of the subject;

measuring a three-dimensional morphological shape of the subject;

detecting a subject and a position/posture of a surgical operation utensil that carries out observation of the subject;

sampling three-dimensional morphological shape information on a site that corresponds to the field of view of the surgical operation utensil from the detected three-dimensional morphological shape information of the subject based on position/posture information on a surgical operation utensil;

sampling three-dimensional information on a site that corresponds to the field of view of the surgical operation utensil from the modified and stored three-dimensional information of the subject based on the detected position/posture information on the surgical operation utensil;

comparing the three-dimensional morphological shape information with the three-dimensional information, thereby outputting a three-dimensional information that is the most analogous to the three-dimensional morphological shape information;

generating data image from the selected, outputted three-dimensional information of the subject; and superimposing and outputting the generated data image and the image of the subject from the surgical operation utensil on each other.

According to a sixth aspect of the present invention, there is provided a surgical operation navigation method, comprising the steps of:

storing three-dimensional information of a subject measured by a medical image diagnosis apparatus;

modifying and storing the stored three-dimensional information of the subject based on predicted modification of the subject;

measuring a three-dimensional morphological shape of the subject;

detecting a subject and a position/posture of a surgical operation utensil that carries out observation of the subject;

sampling two-dimensional morphological shape information on a site that corresponds to the field of view of the surgical operation utensil from the detected three-dimensional morphological shape information of the subject based on position/posture information on a surgical operation utensil;

projecting the site that corresponds to the field of view of the surgical operation utensil from the modified and stored three-dimensional information of the subject, and then, sampling two-dimensional morphological shape information based on position/posture information on the surgical operation utensil;

comparing the two-dimensional morphological shape information and the two-dimensional modification information with each other, selecting two-dimensional modification information that is the most analogous to the two-dimensional morphological shape information, and then, outputting three-dimensional morphological shape information that corresponds to the two-dimensional modification information;

generating data image from the outputted three-dimensional morphological shape information of the subject; and superimposing and outputting the generated data image and the image of the subject from the surgical operation utensil on each other.

DETAILED DESCRIPTION OF THE INVENTION

Hereinafter, preferred embodiments of the present invention will be described with reference to the accompanying drawings.

(First Embodiment)

Figure 1:
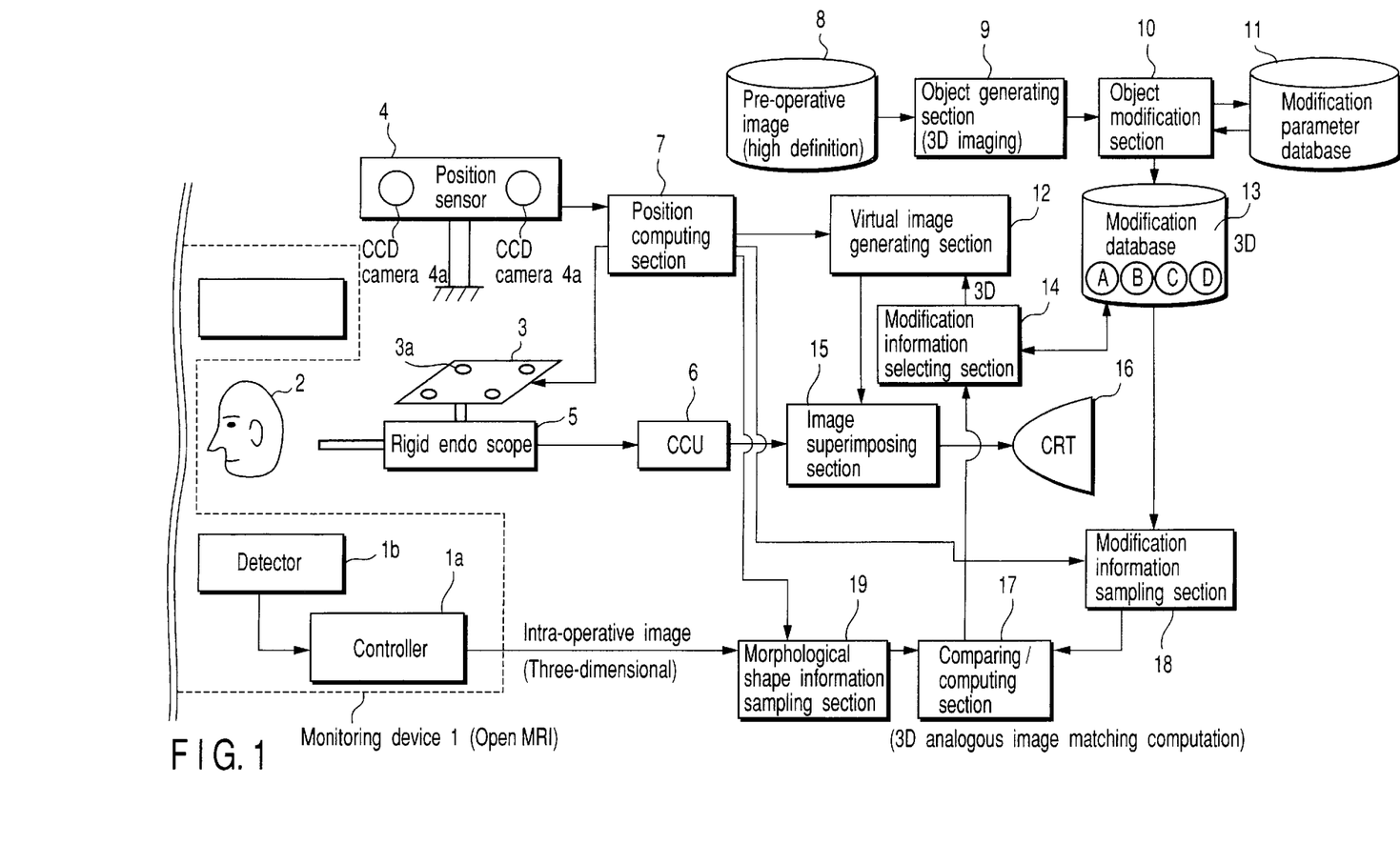
FIG. 1 is a view showing a configuration of a surgical operation navigation apparatus according to a first embodiment of the present invention.

FIG. 1 is a view showing a configuration of a surgical operation navigation apparatus according to a first embodiment of the present invention. In FIG. 1, two-dimensional information (slice image) with high definition, i.e., with high resolution measured by a monitoring device (open MRI) 1 that is a medical image diagnosis apparatus prior to surgical operation is stored in a pre-operative image storage section 8 that is medical image storage section.

An object generating section 9 generates a three-dimensional image from this two-dimensional image.

An object modification section 10 modifies three-dimensional information in a three-dimensional region of interest of a subject set by region-of-interest setting section for setting a three-dimensional region of interest to be processed, by using a modification parameter stored in a modification parameter database 11. A modification object database 13 that is modification information storage section stores these modified three-dimensional images in plurality (A to D).

A controller 1a of the monitoring device 1 functions as three-dimensional morphological shape measuring section for converting an image of a subject 2 detected by a detector 1b during surgical operation into a three-dimensional image.

A position sensor composed of an optical detector 4a such as a CCD camera, a light emitting section 3 composed of a light source 3a such as an LED, and a position computing section 7 configures position/posture detecting section for detecting the subject 2 and a position/posture of a rigid endo scope 5 that is a surgical operation utensil for carrying out observation of the subject 2. As shown in FIG. 1, a position sensor 4 has a plurality of view points. For example, as described in the figure, a plurality of CCD cameras 4a are used, and the position and posture of the rigid endo scope is computed based on a visual difference relevant to (at least three or more) LEDs 3a fixed to the hard mirror from the respective CCD camera 4a.

A morphological shape information sampling section 19 samples three-dimensional morphological shape information on a site that corresponds to the field of view of the hard mirror 5 from the three-dimensional morphological shape information of the subject 2 measured by the controller 1a, based on the position/posture information of the rigid endo scope 5 obtained by the position computing section 7.

On the other hand, a modification information sampling section 18 samples three-dimensional morphological shape information on a site that corresponds to the field of view of the rigid end scope 5 from a modification object database 13 based on the position/posture information on the rigid endo scope 5 obtained by the position computing section 7.

A comparing/computing section 17 compares and computes three-dimensional morphological shape information from the morphological shape information sampling section 19 and the modification information sampling section 18. The modification information selecting section 14 outputs a three-dimensional morphological shape that is the most analogous to the three-dimensional morphological shape information from the morphological shape information sampling section 19 based on the comparison/computation result. The comparing/computing section 17 and the morphological shape information selecting section 14 configures modification shape selecting section.

A virtual image generating section 12 that is data image generating section generates data image from the selected, outputted three-dimensional morphological shape information of the subject.

An image superimposing section 15 superimposes images data image from the virtual image generating section 12 and an image of the subject 2 that is detected by the rigid endo scope 5 and image-processed by a camera control unit (CCU) 6, and outputs the superimposed image to the image display device (CRT) 16.

Figure 3:
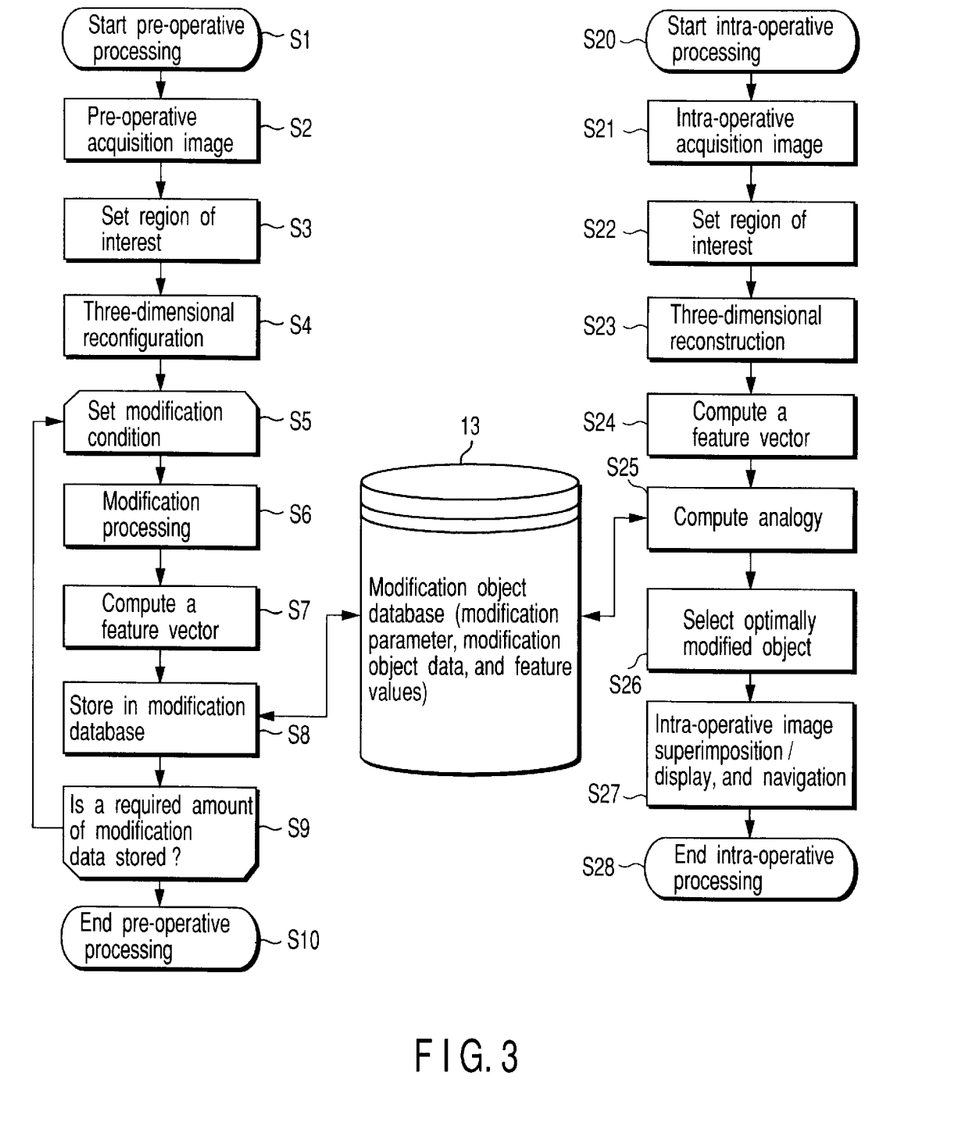
FIG. 3 is a flowchart illustrating an operation of a surgical operation navigation apparatus having a configuration shown in FIG. 1.

FIG. 3 is a flowchart illustrating an operation of a surgical operation navigation apparatus having the above described configuration. First, pre-operative processing will be described here.

When pre-operative processing (step S1) is started, first, a high-definition pre-operative acquisition image (slice image) is measured by a monitoring device (open MRI) 1 (step S2), and the measured image is stored in a pre-operative image storage section 8. Next, a region of interest is set from among the stored pre-operative images, by a region-of-interest setting technique described later (step S3). Then, a three-dimensional image is reconstructed from a two-dimensional image at the object generation section 109 (step S4). Then, a modification condition (modification parameter) concerning predicted modification is set (step S5), and modification processing is applied to a three-dimensional image by referring to the modification condition at an object modification section 10 (step S6).

Then, a characteristic quantity is computed from the modified three-dimensional image (step S7), and the modification object data that is a three-dimensional image, the used modification parameter, and the characteristic quantity are stored in the modification object database 12 (step S8). Here, for example, the characteristic quantity and computation method described later can be employed. When a required number of modification data is stored in the modification object database 13 (step S9), pre-operative processing is terminated (step S10).

Now, intra-operative processing will be described here.

When intra-operative processing is started (step S20), first, an intra-operative acquisition image (slice image) of a subject 2 is measured by a monitoring device (open MRI) 1 (step S21). Next, a region of interest is set from among the pre-operative images by a region-of-interest setting technique described later (step S22). Then, a two-dimensional image of the region of interest is constructed as a three-dimensional image by means of a controller 1a (step S23).

Next, a characteristic quantity is computed from the reconstructed three-dimensional image (step S24), and analogy relevant to the modification object data stored in the modification object database 13 is computed by means of a comparing/computing section 17 (step S25). Here, at the step S24, a characteristic quantity including at least a part of the characteristic quantity obtained at the step S8 is computed. In addition, at the step S25, a three-dimensional image analogy computing method described later is employed. At this time, optimal modification object data is selected based on the analogy computation result (step S26), an image of a subject 2 from a rigid endo scope 5 is superimposed, and the superimposed image is displayed on an image display device (CRT) 16, thereby carrying out navigation (step S27). Then, intra-operative processing is terminated (step S28).

According to the above described first embodiment, subject information is measured in advance by a medical imaging apparatus with its high resolution, and an image can be displayed by using the modified high resolution information, based on morphological shape information with low resolution during surgical operation. Therefore, surgical operation navigation can be carried out in real time based on subject information with high resolution that is hardy measured during surgical operation.

In addition, three-dimensional information on only a site that corresponds to the field of view of a surgical operation utensil is compared, and analogous information is selected. Thus, the degree of analogy can be computed with a smaller amount of computation than when the entire three-dimensional morphological shape information on a subject is compared with three-dimensional information, and data image of a subject can be outputted at a high speed.

(Second Embodiment)

Figure 2:
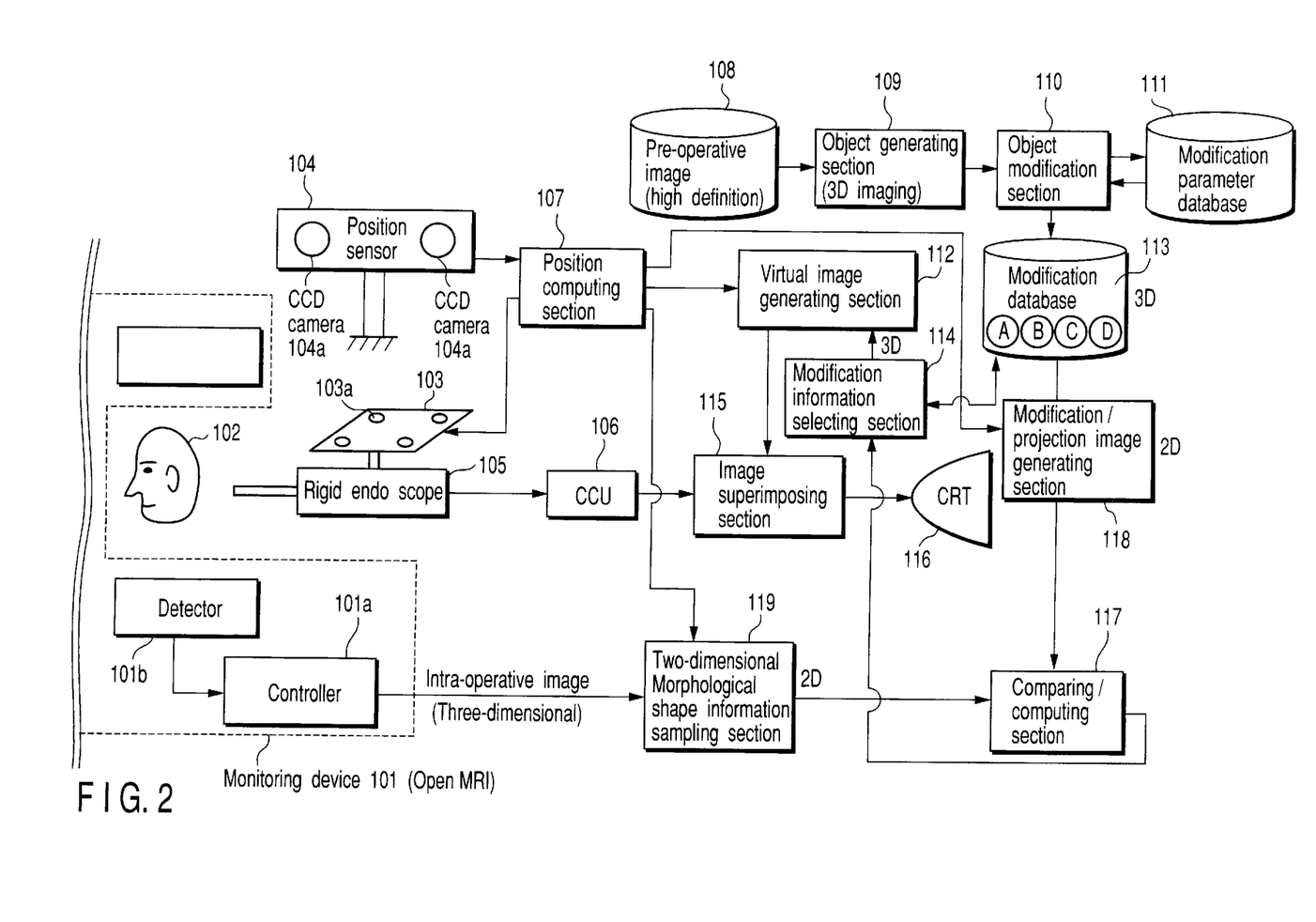
FIG. 2 is a view showing a configuration of a surgical operation navigation apparatus according to a second embodiment of the present invention.

FIG. 2 is a view showing a configuration of a surgical operation navigation apparatus according to a second embodiment of the present invention. In FIG. 2, two-dimensional information (slice image) with high definition, i.e., with high resolution of a subject 2 measured by a monitoring device (open MRI) 101 that is a medical image diagnosis apparatus prior to surgical operation, is stored in a pre-operative image storage section 108 that is medical image storage section. An object generating section 109 generates a three-dimensional image from this two-dimensional image, and delivers the generated image to an object modification section 110.

The object modification 110 modifies three-dimensional information in a three-dimensional region of interest of an object set by region-of-interest setting section for setting a three-dimensional region of interest to be processed, by using a modification parameter stored in a modification parameter database 111. A modification object database 113 that is modification information storage section stores these modified three-dimensional images in plurality (A to D).

A controller 101a of the monitoring device 101 functions as three-dimensional morphological shape measuring section for converting an image of a subject 102 detected by a detector 101b during surgical operation into a three-dimensional image.

A position sensor 104 composed of a detector 104a such as a CCD camera, a light emitting section 103 composed of a light source 103a such as an LED, and a position computing section 107 configure position/posture detecting section for detecting a subject 102 and a position/posture of a hard mirror 105 that is a surgical operation utensil for carrying out observation of the subject 102.

A two-dimensional morphological shape information sampling section 119 samples two-dimensional morphological shape information on a site that corresponds to the field of view of the hard mirror 105, from three-dimensional morphological shape information on the subject 102 measured by the controller 101a, based on the position/posture information on the rigid endo scope 105 obtained by the position computing section 107.

On the other hand, a modification projection image generating section 118 that is two-dimensional modification information sampling section projects a site that corresponds to the field of view of the hard mirror 105 from the modification object database 113, and samples two-dimensional morphological shape information, based on the position/posture information of the rigid endo scope 105 obtained by the position computing section 107.

A comparing/computing section 117 compares and computes two-dimensional morphological shape information from a two-dimensional morphological shape information sampling section 119 and a modification/projection image generating section 118. A modification information selecting section 114 selects two-dimensional modification information that is the most analogous to two-dimensional morphological shape information from a two-dimensional morphological shape information sampling section 119, and outputs three-dimensional morphological shape information that corresponds to the two-dimensional modification information, based on the comparison and computation result.

A virtual image generating section 112 that is data image generating section generates data image from the three-dimensional morphological shape information on the outputted subject 102.

An image superimposing section 115 superimposes data image from the virtual image generating section 112 and the image of the subject 102 that is detected by the rigid endo scope 105 and image-processed by the camera control unit (CCU) 106, and outputs the superimposed image to an image display device (CRT) 116.

Figure 4:
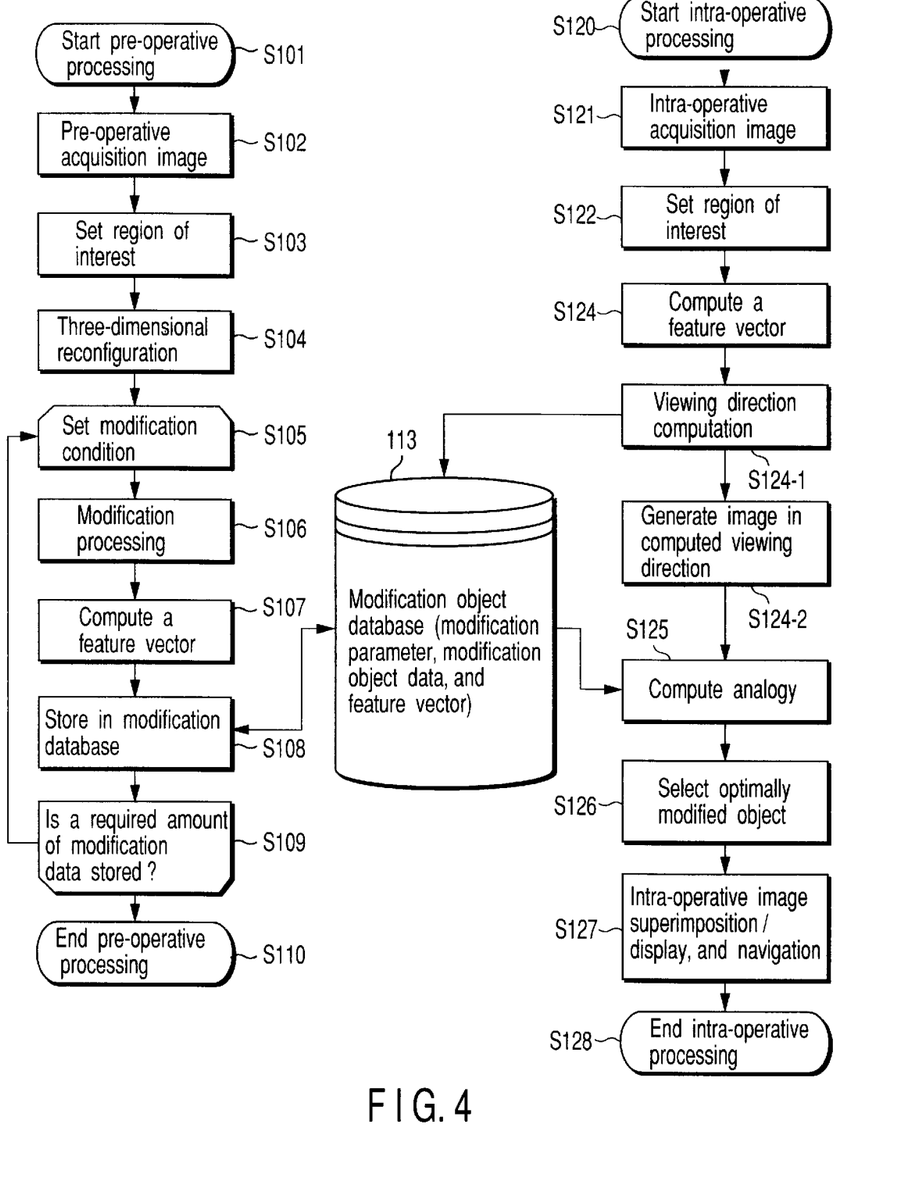
FIG. 4 is a flowchart illustrating an operation of a surgical operation navigation apparatus having a configuration shown in FIG. 2.

FIG. 4 is a flowchart illustrating an operation of a surgical operation navigation apparatus having the above described configuration. The steps S101 to S110 that is pre-operative processing is identical to the previously described steps S1 to S10 in FIG. 3. A duplicate description is omitted here.

Now, intra-operative processing will be described here.

When intra-operative processing is started (step S120), first, an intra-operative acquisition image (slice image) of a subject 102 is measured by a monitoring device (open MRI) 101 (step S121). Next, a region of interest is set from among the pre-operative images by a region-of-interest setting technique described later (step S122). Then, a characteristic quantity of the region of interest is computed from a two-dimensional image of the region of interest (step S124). Then, a viewing direction is computed (step S124-1), and an image in the computed viewing direction is generated (step S124-2). Then, analogy between the generated image and the modification object data stored in the modification object database 13 is computed by a comparing/computing section 117 (step S125). At this time, optimal modification object data is selected based on the analogy computation result (step S126), the image of the subject 102 from the hard mirror 105 is superimposed on the selected data, the superimposed image is displayed on a image display device (CRT) 116, and navigation is carried 0out (step S127), thereby intra-operative processing is terminated (step S128).

According to the above described second embodiment, the analogy between two-dimensional information is compared, and the most analogous modification information is selected. Thus, a quantity of computation is reduced more significantly than a case of computing the degree of analogy of three-dimensional information. Therefore, data image can be outputted at a high speed.

Hereinafter, a three-dimensional region-of-interest setting technique will be described. Although there are various techniques of setting a three-dimensional region of interest, the following techniques (1), (2), (3), and (4) are mainly employed.

In these techniques (1), (2), (3), and (4) each, processing is carried out by interactively making operation by a pointing device such as a mouse while a user is observing a slice image or a three-dimensional image on a display section of a display device such as a CRT 16.

In technique (1), volume data is displayed on a CRT 16 for each slice image, and a region of interest is set by using a pointing device on the slice image, the region of interest on the slice image is repeatedly set relevant to all the slice images, and the region of interest relevant to all the slice images is set, whereby a three-dimensional region of interest is set as the entire volume data.

In technique (2), thresholds of the upper and lower limits of pixel values are assigned to a slice image, whereby the image can be two-valued. Further, the upper and lower limits are assigned in a plurality of sets, whereby the image can be multiply valued.

By doing this, after the image has been divided into a plurality of regions, a region required by the user is pointed by a pointing device, and the region of interest is set.

In technique (3), each slice is subjected to image segmentation based on edge information, and a region including a region of interest is sampled by pointing it by a pointing device, setting the region of interest.

In this technique, a region is specified relevant to a slice distant by some slices other than a region specified for each slice, and the region may be automatically sampled by a region extension technique when the region-of-interest sampled slice image is defined as a reference with respect to an intermediate slice image.

In technique (4), volume data is subjected to three-dimensional rendering by a volume rendering or surface rendering technique, a point included in a region of interest is pointed by a pointing device in this rendering window, certain thresholds are defined based on the pixel value of the specified point, a region in which a difference in pixel values is within the thresholds is defined as a region of interest, and the defined region is set as a three-dimensional object region.

Then, raw volume data is processing by these techniques (1), (2), (3), and (4) or the like, and the processed data is set as three-dimensional region-of-interest volume data, whereby a three-dimensional region of interest is set.

When the region of interest is sampled by the above techniques, a nose region may be sampled. However, in such a case, a device for eliminating such noise region is provided.

For example, when a region smaller than a predetermined side is sampled by making judgment based on the region size, such region may be recorded as a noise.

Now, a method for computing a three-dimensional characteristic quantity of a region of interest relevant to a three-dimensional image set by the above described technique will be described here.

At this time, as three-dimensional geometrical features, there are employed: three-dimensional position coordination P (x, y, z) of a gravity in region of interest; a volume V in region of interest; surface area S for region of interest; value of ratio s $^{1/2}$/v $^{1/3}$ between a volume and a surface area as a parameter representing morphological complex; a ratio of lengths of three main axes when they are elliptically approximated as parameters representing a three-dimensional direction in region of interest; and directional vector or the like.

In addition, as texture features, there are employed: a commonly generated matrix expressed by formula (1); a directional secondary moment computed by the commonly generated matrix, and indicated by formula (2). In addition, as three-dimensional Fourier features, there are employed MPS (Metric Pattern Signature) expressed by formula (3) and APS (Angular Pattern Signature) expressed by formula (4) or the like.

$$P\delta(k, l); \delta=(\delta x, \delta y, \delta z) \quad (1)$$

where "k" and "l" denote pixel values, which represents a probability of simultaneously generating an event in which a pixel value having a pixel distant by $\delta=(\delta x, \delta y, \delta z)$ is "l" from the standpoint of a pixel having a pixel value "k".

$$\sum_k \sum_l \{P_\delta(k, l)\}^2 \quad (2)$$

$$p(r) = \sum_\theta \sum_\varphi P(r, \theta, \phi) \quad (3)$$

$$q(r) = \sum_\theta \sum_\varphi P(r, \theta, \phi) \quad (4)$$

In formulas (3) and (4), P (r, θ, φ) is a function that displays as an extreme coordinate a power spectrum of a value in a spatial frequency region after three-dimensional Fourier transform.

Any of the feature values computed by features sampling processing as described above are specific features having a three-dimensional image. Any value may be used as long as it represents three-dimensional features.

Now, a technique for computing three-dimensional image analogy will be described. First, a characteristic weighting coefficient is set. That is, the degrees of importance of features each are considered, thereby making it possible to obtain the search result reflected by the user's intention.

For example, if a weighting coefficient is increased, and search is applied by taking importance of a feature which is a volume in region of interest, a volume analogous image can be efficiently searched.

In this processing as well, all the feature values computed on the CRT 16 are displayed, and interactive display for setting the weighting coefficient of features each is carried out, whereby the weighting coefficient is set based on arbitrary setting of the user.

Here, the weighting coefficients each can be set with respect to features each, and further, can be set for groups by features.

Figure 5:
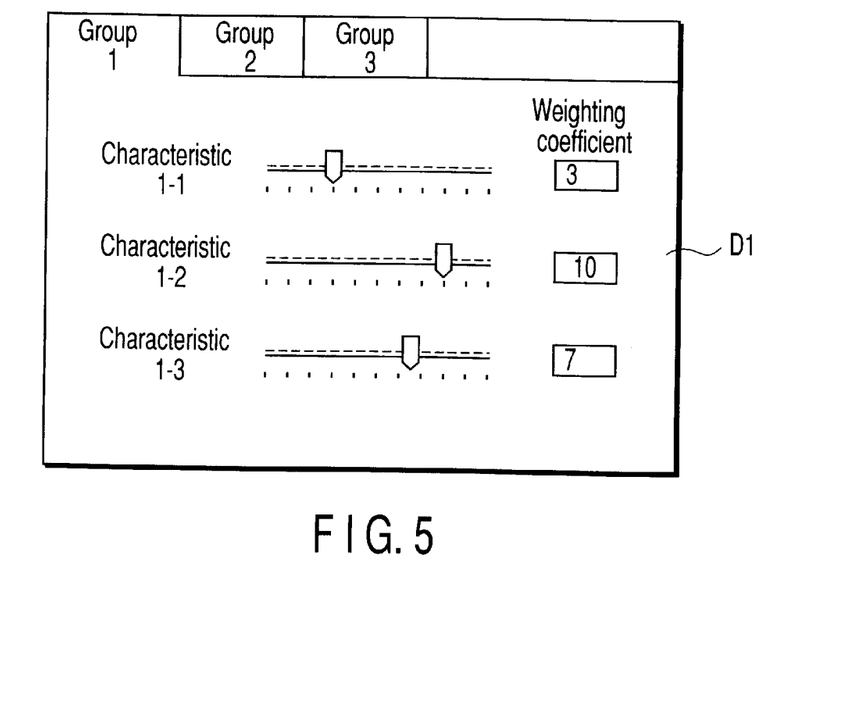
FIG. 5 is a view showing a dialog box D1 for setting a weighting coefficient concerning each of the features of the present invention.

FIG. 5 shows a dialog box D1 for setting the weighting coefficients concerning features each.

That is, in this case, the value of weighting coefficient can be set by the dialog box D1 displayed on the CRT 16 by using a pointing device such as a mouse.

Figure 6:
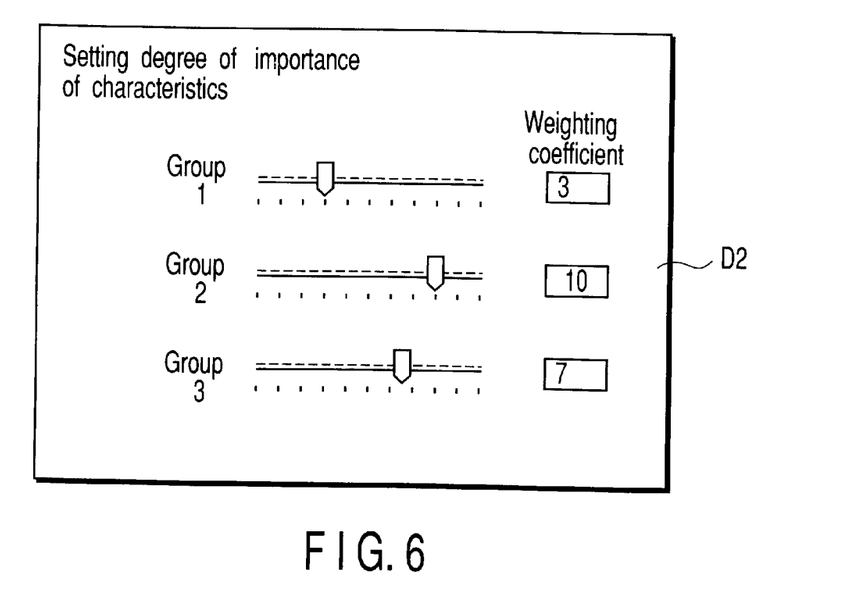
FIG. 6 is a view showing a dialog box D2 for setting a weighting coefficient to each group.

FIG. 6 shows a dialog box D2 for setting the weighting coefficient relevant to each group.

That is, in this case, the weight coefficient relevant to each group can be set by a dialog box D2 displayed on the CRT 16 by using a pointing device such as a mouse.

Here, the condition settings of classification of features or weighting coefficients of each features are assigned as combinations preset as an initial condition, making it possible to apply searching while such initial condition is set or making it possible for a user to carry out arbitrary settings by using processing for setting classification of features or weighting coefficients of each features.

Next, in processing for computing the degree of analogy, search is executed in accordance with the set condition.

Assuming that the feature values computed by the above feature computation processing is M (f1 to fM), and the data in a database that carries out search is N (I1 to IN), when the feature matrix is represented by formula (5), a feature vector of "q" three-dimensional images Iq is expressed by formula (6).

In formula (6), each feature term is normalized by multiplying "k".

$$F = \begin{pmatrix} F_{11} F_{12} & \cdots & F_{1p} & \cdots & F_{1M} \\ F_{21} & & & & \\ \vdots & & \vdots & & \\ F_{q1} & & F_{qp} & & \\ \vdots & & \vdots & & \\ F_{N1} & & & & F_{NM} \end{pmatrix} \quad (5)$$

$$\vec{f_q} = \sum_{j=1}^{M} w_j \cdot \{D(k_j \cdot F_{qj}) - k_j \cdot \overline{F_j}\} \cdot \vec{ij} \quad (6)$$

where each term in the formula is as follows:

$$\overline{F_p} = \frac{1}{N} \sum_{j=1}^{N} F_{jp}, \; v_p = \frac{1}{N} \sum_{j=1}^{N} (F_{jp} - \overline{F_p})^2,$$

-continued $$\sigma_p = \sqrt{v_p}, \; k_p = \frac{1}{\sigma_p}, \; D_{(x)} \begin{cases} x|x| \le d \\ d|x| > d \end{cases}$$

where "d" denotes a value defined as another proper value, and "wj" denotes the weighting coefficient of each features.

The degree of analogy can be defined by the characteristic vector shown in formula (6).

That is, when an image targeted for search is Ip, the function for the degree of analogy relevant to another image Iq in the database 5 is expressed by formula (7)

$$\text{Sim}(p, q) = |\vec{f_q} - \vec{f_p}|^2 \quad (7)$$

As a result, the analogy increases as Sim (p, q) decreases.

In this way, this function is computed for all the images contained in a database, thereby making it possible to determine the sequence of degree of analogy.

The feature values defined in formula (6) is considered based on classification of features made by the above classification of characteristics. If feature grouping is carried out, the weighting coefficient $W_j$ multiplied for each feature term is changed to $W_G(j) \cdot W_j$, thereby obtaining a definition formula of the feature values having the settings for grouping reflected thereon.

However, $W_G(j)$ is a weighting coefficient of a group containing "j" feature "fj".

According to the present invention, subject information is measured in advance by a medical imaging apparatus with its high resolution, and an image can be displayed by using the modified high resolution information, based on morphological shape information with low resolution during surgical operation. Thus, surgical operation navigation can be carried out in real time based on subject information with its high resolution that is hardly measured during surgical operation.

In addition, according to the present invention, three-dimensional information on only a site that corresponds to the field of view of a surgical operation utensil is compared, and analogous information is selected. Thus, the degree of analogy can be computed with a smaller amount of computation than when the entire three-dimensional morphological shape information on a subject is compared with the three-dimensional information, and data image of the subject can be outputted at a high speed.

Further, according to the present invention, the degrees of analogy between two-dimensional information are compared, and the most analogous morphological shape information is selected. Thus, an amount of computation is smaller than a case of computing the degree of analogy of three-dimensional information. Therefore, data image can be outputted at a high speed.

What is claimed is:

1. A surgical operation navigation apparatus, comprising:
    medical image storage section for storing three-dimensional information of a subject measured by medical image diagnosis apparatus;
    modification information storage section for modifying and storing three-dimensional information of the subject stored in the medical image storage section based on predicted modification of the subject;
    morphological shape measuring instrument for measuring a three-dimensional morphological shape of the subject;

position/posture detecting section for detecting a subject and a position/posture of a surgical operation utensil that carries out observation of the subject;

modified morphological shape selecting section for comparing a three-dimensional morphological shape of the subject measured by the morphological shape measuring instrument with three-dimensional information stored in the modification information storage section, thereby selecting and outputting three-dimensional information of the subject which is the most analogous to a morphological shape of the subject from the modification information storage section;

data image generating section for generating data image from the selected, outputted three-dimensional information of the subject; and image superimposing section for superimposing the data image from the data image generating section and the image of the subject from the surgical operation utensil on each other, thereby outputting the superimposed image to an image display device.

2. A surgical operation navigation apparatus according to claim 1, wherein resolution of the medical image diagnosis apparatus is higher than that of the morphological shape measuring instrument.

3. A surgical operation navigation apparatus according to claim 1, wherein the medical image diagnosis apparatus measures information of a subject prior to surgical operation, and the morphological shape measuring instrument measures a morphological shape of the subject during the surgical operation.

4. A surgical operation navigation apparatus according to claim 1, further comprising region-of-interest setting section for a three-dimensional region of interest to be processed in three-dimensional information of a subject stored in the medical image storage section, wherein the morphological shape information storage section modifies and stores three-dimensional information in a three-dimensional region of interest of a subject set at the region-of-interest setting section.

5. A surgical operation navigation apparatus according to claim 1, comprising section for sampling and weighting a characteristic quantity from the modified three-dimensional information.

6. A surgical operation navigation apparatus, comprising:

medical image storage section for storing three-dimensional information of a subject measured by a medical image diagnosis apparatus;

modification information storage section for modifying and storing three-dimensional information of the subject stored in the medical image storage section based on predicted modification of the subject;

morphological shape measuring instrument for measuring a three-dimensional morphological shape of the subject;

position/posture detecting section for detecting a subject and a position/posture of a surgical operation utensil that carries out observation of the subject;

morphological shape information sampling section for sampling three-dimensional morphological shape information on a site that corresponds to the field of view of the surgical operation utensil from three-dimensional morphological shape information of the subject measured by the morphological shape measuring instrument based on position/posture information on a surgical operation utensil from the position/posture detecting section;

modification information sampling section for sampling three-dimensional morphological shape information on a site that corresponds to the field of view of the surgical operation utensil from the modification information storage section based on position/posture information on the surgical operation utensil from the position/posture section;

modification information selecting section for comparing the morphological shape information sampling section with three-dimensional morphological shape information from the modification information sampling section, thereby selecting from the modification information sampling section a three-dimensional shape that is the most analogous to the morphological shape information from the morphological shape information sampling section;

data image generating section for generating data image from the selected, outputted three-dimensional morphological shape information of the subject; and image superimposing section for superimposing data image from the data image generating section and an image of the subject from the surgical operation utensil on each other, followed by outputting the superimposed image to an image display device.

7. A surgical operation navigation apparatus according to claim 6, wherein resolution of the medical image diagnosis apparatus is higher than that of the morphological shape measuring instrument.

8. A surgical operation navigation apparatus according to claim 6, wherein the medical image diagnosis apparatus measures information of a subject prior to surgical operation, and the morphological shape measuring instrument measures a morphological shape of the subject during the surgical operation.

9. A surgical operation navigation apparatus according to claim 6, further comprising region-of-interest setting section for a three-dimensional region of interest to be processed in three-dimensional information of a subject stored in the medical image storage section, wherein the morphological shape information storage section modifies and stores three-dimensional information in a three-dimensional region of interest of a subject set at the region-of-interest setting section.

10. A surgical operation navigation apparatus according to claim 6, comprising section for sampling and weighting a feature value from the modified three-dimensional information.

11. A surgical operation navigation apparatus, comprising:

medical image storage section for storing three-dimensional information of a subject measured by a medical image diagnosis apparatus;

modification information storage section for modifying and storing three-dimensional information of the subject stored in the medical image storage section based on predicted modification of the subject;

morphological shape measuring instrument for measuring a three-dimensional morphological shape of the subject;

position/posture detecting section for detecting a subject and a position/posture of a surgical operation utensil that carries out observation of the subject;

two-dimensional morphological shape information sampling section for sampling two-dimensional morphological shape information on a site that corresponds to the field of view of the surgical operation utensil from three-dimensional morphological shape information of the subject measured by the morphological shape measuring instrument based on position/posture information on a surgical operation utensil from the position/posture detecting section;

two-dimensional modification information sampling section for projecting the site that corresponds to the field of view of the surgical operation utensil from the modification information storage section, and then, sampling two-dimensional morphological shape information based on position/posture information on the surgical operation utensil from the position/posture detecting section;

modification information selecting section for comparing two-dimensional morphological shape information from the two-dimensional morphological shape information sampling section and the two-dimensional modification information sampling section with each other, selecting two-dimensional modification information that is the most analogous to two-dimensional morphological shape information from the two-dimensional morphological shape information sampling section, and then, outputting three-dimensional morphological shape information that corresponds to the two-dimensional modification information;

data image generating section for generating data image from the selected, outputted three-dimensional morphological shape information of the subject; and image superimposing section for superimposing the data image from the data image generating section and the image of the subject from the surgical operation utensil on each other, followed by outputting the superimposed image data to an image display device.

12. A surgical operation navigation apparatus according to claim 11, wherein resolution of the medical image diagnosis apparatus is higher than that of the morphological shape measuring instrument.

13. A surgical operation navigation apparatus according to claim 11, wherein the medical image diagnosis apparatus measures information of a subject prior to surgical operation, and the morphological shape measuring instrument measures a morphological shape of the subject during the surgical operation.

14. A surgical operation navigation method, comprising the steps of:

storing three-dimensional information of a subject measured by a medical image diagnosis apparatus;

modifying and storing the stored three-dimensional information of a subject based on predicted modification of the subject;

measuring a three-dimensional morphological shape of the subject;

detecting a subject and a position/posture of a surgical operation utensil that carries out observation of the subject;

comparing the measured three-dimensional morphological shape of the subject with the stored three-dimensional information, thereby selecting and outputting three-dimensional information of the subject which is the most analogous to a morphological shape of the subject;

generating data image from the selected, outputted three-dimensional information of the subject; and superimposing and displaying the generated data image and the image of the subject from the surgical operation utensil on each other.

15. A surgical operation navigation method according to claim 14, wherein resolution of the medical image diagnosis apparatus is higher than that of the morphological shape measuring step.

16. A surgical operation navigation method according to claim 14, wherein the medical image diagnosis apparatus measures information of a subject prior to surgical operation, and the morphological shape measuring step measures a morphological shape of the subject during the surgical operation.

17. A surgical operation navigation method according to claim 14, further comprising region-of-interest setting step for setting a three-dimensional region of interest to be processed to the stored three-dimensional information of a subject, wherein the morphological shape information storage step modifies and stores three-dimensional information in the set three-dimensional region of interest of a subject.

18. A surgical operation navigation method according to claim 14, comprising a step for sampling and weighting a characteristic quantity from the modified three-dimensional information.

19. A surgical operation navigation method, comprising the steps of:

storing three-dimensional information of a subject measured by a medical image diagnosis apparatus;

modifying and storing the stored three-dimensional information of the subject based on predicted modification of the subject;

measuring a three-dimensional morphological shape of the subject;

detecting a subject and a position/posture of a surgical operation utensil that carries out observation of the subject;

sampling three-dimensional morphological shape information on a site that corresponds to the field of view of the surgical operation utensil from the detected three-dimensional morphological shape information of the subject based on position/posture information on a surgical operation utensil;

sampling three-dimensional information on a site that corresponds to the field of view of the surgical operation utensil from the modified and stored three-dimensional information of the subject based on the detected position/posture information on the surgical operation utensil;

comparing the three-dimensional morphological shape information with the three-dimensional information, thereby outputting a three-dimensional information that is the most analogous to the three-dimensional morphological shape information;

generating data image from the selected, outputted three-dimensional information of the subject; and superimposing and outputting the generated data image and the image of the subject from the surgical operation utensil on each other.

20. A surgical operation navigation method according to claim 19, wherein resolution of the medical image diagnosis apparatus is higher than that of the morphological shape measuring step.

21. A surgical operation navigation method according to claim 19, wherein the medical image diagnosis apparatus measures information of a subject prior to surgical operation, and the morphological shape measuring step measures a morphological shape of the subject during the surgical operation.

22. A surgical operation navigation method according to claim 19, further comprising region-of-interest setting step for setting a three-dimensional region of interest to be processed to the stored three-dimensional information of a subject, wherein the morphological shape information storage step modifies and stores three-dimensional information in the set three-dimensional region of interest of a subject.

23. A surgical operation navigation method according to claim 19, comprising a step for sampling and weighting a feature value from the modified three-dimensional information.

24. A surgical operation navigation method, comprising the steps of:
  storing three-dimensional information of a subject measured by a medical image diagnosis apparatus;
  modifying and storing the stored three-dimensional information of the subject based on predicted modification of the subject;
  measuring a three-dimensional morphological shape of the subject;
  detecting a subject and a position/posture of a surgical operation utensil that carries out observation of the subject;
  sampling two-dimensional morphological shape information on a site that corresponds to the field of view of the surgical operation utensil from the detected three-dimensional morphological shape information of the subject based on position/posture information on a surgical operation utensil;
  projecting the site that corresponds to the field of view of the surgical operation utensil from the modified and stored three-dimensional information of the subject, and then, sampling two-dimensional morphological shape information based on position/posture information on the surgical operation utensil;
  comparing the two-dimensional morphological shape information and the two-dimensional modification information with each other, selecting two-dimensional modification information that is the most analogous to the two-dimensional morphological shape information, and then, outputting three-dimensional morphological shape information that corresponds to the two-dimensional modification information;
  generating data image from the outputted three-dimensional morphological shape information of the subject; and
  superimposing and outputting the generated data image and the image of the subject from the surgical operation utensil on each other.

25. A surgical operation navigation method according to claim 24, wherein resolution of the medical image diagnosis apparatus is higher than that of the morphological shape measuring step.

26. A surgical operation navigation method according to claim 24, wherein the medical image diagnosis apparatus measures information of a subject prior to surgical operation, and the morphological shape measuring step measures a morphological shape of the subject during the surgical operation.

* * * * *